United States Patent
Roeck et al.

(10) Patent No.: US 9,456,749 B2
(45) Date of Patent: Oct. 4, 2016

(54) PORTABLE ELECTRONIC DEVICE WITH KETONE SENSOR

(71) Applicant: Sensirion AG, Stafa (CH)

(72) Inventors: Frank Roeck, Wil (CH); Moritz Lechner, Uerikon (CH); Michael Dommer, Buchs (CH)

(73) Assignee: Sensirion AG, Stafa (CH)

( * ) Notice: Subject to any disclaimer, the term of this patent is extended or adjusted under 35 U.S.C. 154(b) by 387 days.

(21) Appl. No.: 14/161,114

(22) Filed: Jan. 22, 2014

(65) Prior Publication Data

US 2014/0228698 A1    Aug. 14, 2014

(30) Foreign Application Priority Data

Jan. 31, 2013 (EP) .................................... 13405025

(51) Int. Cl.

| | |
|---|---|
| *A61B 5/08* | (2006.01) |
| *A61B 5/00* | (2006.01) |
| *G01N 33/497* | (2006.01) |
| *A61B 5/083* | (2006.01) |

(52) U.S. Cl.
CPC ............. *A61B 5/0004* (2013.01); *A61B 5/083* (2013.01); *G01N 33/497* (2013.01); *G01N 2033/4975* (2013.01)

(58) Field of Classification Search
None
See application file for complete search history.

(56) References Cited

U.S. PATENT DOCUMENTS

| | | | |
|---|---|---|---|
| 8,280,436 B2 | 10/2012 | Harris, Jr. | |
| 2003/0044997 A1* | 3/2003 | Kasahara | G01N 33/5438 436/149 |
| 2006/0277974 A1* | 12/2006 | Gouma | G01N 27/12 73/25.03 |
| 2007/0020934 A1* | 1/2007 | Gaidis | H01L 21/0332 438/689 |
| 2008/0077037 A1 | 3/2008 | Gouma et al. | |
| 2009/0054799 A1* | 2/2009 | Vrtis | G01N 33/497 600/532 |
| 2009/0126460 A1* | 5/2009 | Gardner | G01N 33/0031 73/31.06 |
| 2012/0231841 A1 | 9/2012 | Niederberger et al. | |
| 2013/0165806 A1* | 6/2013 | Wondka | A61B 5/0816 600/532 |

FOREIGN PATENT DOCUMENTS

| | | |
|---|---|---|
| WO | 9519563 | 7/1995 |
| WO | 0193743 | 12/2001 |
| WO | 2012087187 | 6/2012 |
| WO | 2012100362 | 8/2012 |

OTHER PUBLICATIONS

S. K. Kundu et al., "Breath Acetone Analyzer: Diagnostic Tool to Monitor Dietary Fat Loss" Clinical Chemistry, vol. 39, No. 1, 1996, 87-92.

Y. Yamada, and S. Hiyama, "Breath Acetone Analyzer to Achieve Biochip Mobile Terminal", NTT Docomo Technical Journal, Technology Reports, 2012, vol. 14, No. 1, pp. 51-57.

* cited by examiner

*Primary Examiner* — Etsub Berhanu
(74) *Attorney, Agent, or Firm* — Cooper & Dunham LLP

(57) ABSTRACT

A portable electronic device is described with telecommunication capabilities to allow for data and/or voice communication via private or public networks, having an integrated chemical sensor sensitive to ketones within a breath sample of a user wherein the sensor comprises at least one metal oxide gas sensor and a control circuit for the sensor integrated onto a common substrate or package.

11 Claims, 3 Drawing Sheets

PORTABLE ELECTRONIC DEVICE WITH KETONE SENSOR

FIELD OF THE INVENTION

The present invention relates to a portable electronic device such as a mobile phone, tablet and the like with an integrated chemical sensor for detecting the presence of ketones in the breath.

BACKGROUND OF THE INVENTION

Portable or mobile devices originally introduced as mobile phones or electronic agendas become more and more ubiquitous. As the processing power of their internal processors grows and equally the bandwidth for communication with stationary processors, such portable devices take on more and more the role of multi-purpose tools available to consumers and specialist users alike.

It has been recognized that portable devices can benefit from the presence of sensors capable of providing a chemical analysis of materials brought into contact or the vicinity of the device. Whilst there are many possible applications for such sensors, it suffices to consider for example the analysis of air surrounding the portable device. Such an analysis can be useful for multiple purposes such as testing for hazardous gases, breath analysis for general medical purposes or driving fitness, and the like.

Specialized devices for testing the breath for ketones are well known and can for example be found in the United States patent application 2008/0077037.

Recently progress towards portable devices have been reported in the NTT DOCOMO Technical Journal Vol. 14, No. 1,51-57. However, the described device remains a specialized equipment, which can communicated with remote servers only via a separate mobile phone.

Acetone detection integrated in a mobile device is briefly referred to in the U.S. Pat. No. 8,280,436 B2 purporting to use infrared spectrophotometers, electrochemical fuel cells or other gas analysers. The acetone is used as an indicator for the blood alcohol levels of the user.

In clinical studies such as S. K. Kundu et al., "Breath Acetone Analyzer: Diagnostic Tool to Monitor Dietary Fat Loss" CLINICAL CHEMISTRY, Vol. 39, No. 1, 1993, 87-92 correlations have been suggested between acetone measurements and fat loss.

It has further been recognized that devices which receive a mixture of breath and surrounding air require compensation for the dilution caused by the air The compensation can done using parallel humidity, chemical (e.g. CO2, O2 concentrations) or temperature measurements using for example optical or other methods.

Humidity sensors for mobile applications are described for example in the published United States patent application US 2012/231841 and ways of manufacturing miniaturized sensors as MEMS devices with a CMOS connections and circuitry are described for example in the published international patent applications WO 2012/100362 A1 or WO 95/19563.

In view of the prior art it is an object of the present invention to improve general purpose portable devices with an integrated ketone analyzer sufficiently small to fit within the housing of such devices.

SUMMARY OF THE INVENTION

Hence, according to a first aspect of the invention, there is provided a portable electronic device, preferably with telecommunication capabilities to allow for data and/or voice communication via private or public networks, with an integrated chemical sensor sensitive to ketones, particularly acetone, within a breath sample of a user wherein the sensor comprises at least one metal oxide gas sensor and a control circuit for the sensor integrated onto a common substrate or package.

The metal oxide gas sensor includes preferably tungsten oxide W03 and even more preferably silicon doped tungsten oxide Si:W03.

Preferably the device includes a local processor or communication devices to access a remote processor for deriving an indicator for metabolic ketosis or fat burning of the user, preferably linked to a display driver for displaying a signal representative of the presence of fat burning on a display of the device. The same or another display driver can also be used for displaying a signal representative of the presence of ketones on a display of the device.

The representation or display can be qualitatively in form of, for example, a color signal indicating to the user the presence or absence by a change of color or the display of a respective message.

The representation of the fat burning can also be quantitative by using a converter which applies for example a linear correlation between the acetone content in the breath and the body fat loss.

The circuit is preferably implemented using a CMOS process or a CMOS compatible process such that leads connecting the metal oxide sensor to the control circuit use metal layers of the CMOS substrate. In a preferred variant of this embodiment, a heater used to heat the metal oxide gas sensor is also connected to metal layers of the CMOS substrate. Using such an integrated design, it is possible to reduce the size of the sensor and the integrated control circuit to less the 5 mm by 5 mm, preferably even less than 2 mm by 2 mm.

The reduced size facilitates the integration into a portable electronic device, such that in a preferred embodiment the sensor and the control circuit can be enclosed in a housing having an air duct with an opening to the exterior of the housing connecting the chemical sensor to the outside and with the total area of the opening being sufficiently small to act as restriction to diffusion, such as 10 square millimeters or 3.14 square millimeters or even less. Such integration is seen as important as for general purpose devices it is often not acceptable to have external tubes connected to the housing of the device.

The integration into the housing of a portable device with data communication capabilities can be used to communicate measured raw data or processed data from the sensor to be sent to remote locations for further processing. Based on preference settings selected by the user, the transmittal can be automated by allowing the processing unit of the device to access the registers or memory location at which the sensor data are stored. The processing at a remote location can be used to improve the measurement or generate user alerts to be transmitted back the device.

As the device is preferably tubeless, it preferably includes a compensator for compensating for the effect of variations in the amount of exhaled breath passing the opening.

The diffusion restriction can be regarded as acting as impedance to an instantaneous establishment of an equilibrium of the air in front and behind the opening. Thus any changes in the composition of the air propagate into the housing with a delay. Under the normal operating conditions of a typical mobile device, this delay exceeds the time during which the air is moved and exchanged around the device or the acceptable time limit for a user to receive a result of the measurement. Without compensation a measurement would thus result in a lower value than the true value.

In a preferred embodiment of the invention, the compensator is connected to the output of at least one additional sensor sensitive to conditions in the space behind the opening to correct for dilution of exhaled breath by ambient air at the outside of the opening, such as a sensor for humidity, temperature, or carbon dioxide or oxygen concentration.

In a further preferred embodiment of the invention, the compensator corrects the signal representative of a concentration of the component or an initial or intermediate value of a measured concentration with a static or dynamic factor representing the geometry of the opening and/or the duct.

To increase the accuracy of the measurement the above devices for compensating for the dilution and for the geometry of the opening and/or the duct are best combined and applied both to a measurement.

The portable device can be a smart phone, a handheld computer, a laptop, an electronic reader, a tablet computer, a game controller, a pointing device, a photo or a video camera, digital music player, wrist watch, key fob, head set or a computer peripheral. Its housing is typically a shell of metal, glass, or plastic material and can be assembled as a unibody or from several parts. Enclosed in the housing are typically processors, drivers for parts such as screens, antennae, cameras, microphones and speakers as well as batteries to provide power to the device and its parts. A screen is typically arranged as a part of the housing or mounted behind a transparent window of the housing.

The above and other aspects of the present invention together with further advantageous embodiments and applications of the invention are described in further details in the following description and figures.

DETAILED DESCRIPTION

Figure 1A:
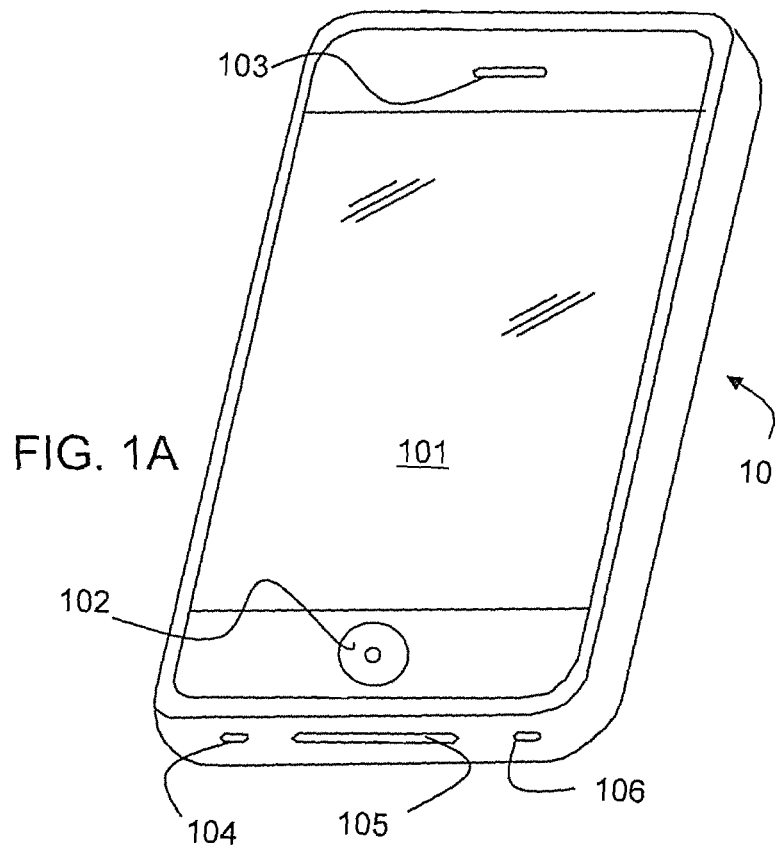
FIG. 1A is a perspective view of a portable electronic device.

The device of FIG. 1A is a portable electronic device such as a mobile phone with telecommunication capabilities (not shown) to allow for data and/or voice communication via private or public networks. The housing 10 of the mobile phone includes a front side with a screen 101 and elements like buttons 102 to let a user interact with the phone. Also shown on the front side is an opening 103 for a loudspeaker. Further openings 104,105 are located at a lower side wall of the housing 10. It is well known to mount components like microphones and loudspeakers behind such openings.

Figure 1B:
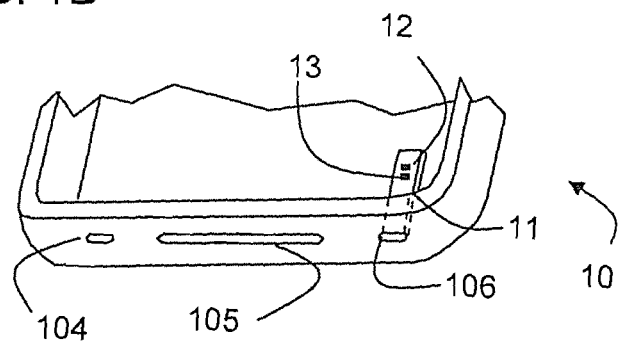
FIG. 1B is a schematic view into part of the housing of the device of FIG. 1A.

Another opening 106 is located at the lower side wall. As shown in FIG. 1B the opening 106 is linked to a tubular duct 11 passing through the interior of the housing. A chemical sensor 12 and a humidity sensor 13 are both mounted along the duct 11 such that the sensitive areas of both sensors are essentially exposed air of the same composition entering the duct through the opening 106. The actual size and shape of the duct 11 depends on the volume available and the nature of the chemical sensor 12 and the humidity sensor 13 can vary, but given the physical constraints of portable mobile devices the diameter of the opening is typically in the range of less than 2 mm and in the present example actually about 1 mm.

In the example the chemical sensor is a gas sensor using a metal-oxide layer mounted onto and integrated with a CMOS substrate. The metal-oxide used can be for example tin oxide, tungsten oxide, gallium oxide, indium oxide, zinc oxide, in particular silicon doped tungsten oxide. However the sensor material can also be based on tin oxide, gallium oxide, indium oxide, or zinc oxide. For particular embodiments as described in further details below the sensor can also include a micro electro-mechanical system or MEMS type heat source integrated within the sensor. The sensor is integrated with its own CMOS circuitry for control and read-out. The physical dimensions of the sensor including the CMOS circuit and the MEMS sensor is less than 2 mm×2 mm. Alternatively the sensor and the circuit can be on separate substrates but cast into a single package.

The chemical and humidity sensors 12, 13 can be manufactured as described for example in the cited application WO 2012/100362. The humidity sensor is best combined with a temperature sensor. Such sensors are commercially available, e.g. from Sensirion™ under the trade name SHTC1. The SHTC1 sensor measures 2 mm×2 mm×0.8 mm. Both sensors can for example be mounted adjacent to each other in the duct 11.

Figure 2A:
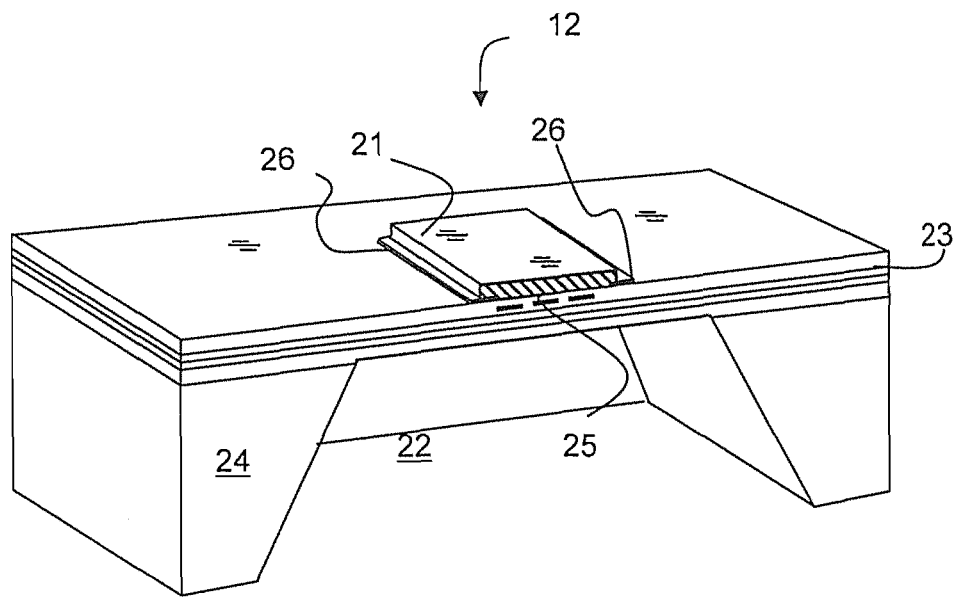
FIG. 2A is a schematic perspective view of a metal oxide gas sensor in accordance with an example of the present invention.
Figure 2B:
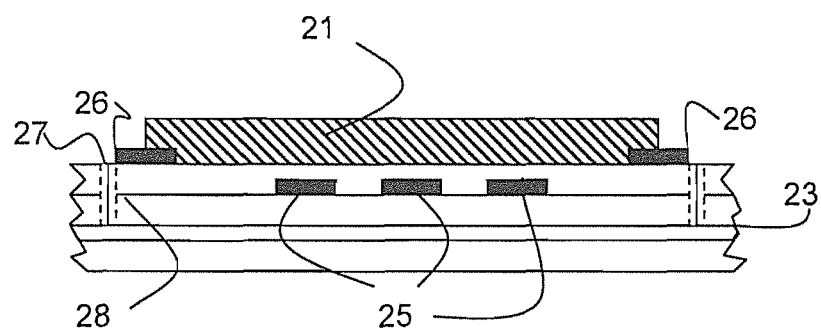
FIG. 2B is schematic cross-section of the sensor of FIG. 2A.

An enlarged part of the gas sensor 12 is shown in FIGS. 2A and 2B. The gas sensor has a sensing layer 21 of tungsten oxide. The sensor is integrated with a CMOS circuitry (not shown) on a single substrate. Parts of the CMOS layers 23 and handle layer 24 required for the CMOS circuit are etched away to form a cavity 22 at the location of the sensor. The remaining layers 23 form a thin membrane to support the actual sensor 12.

Embedded within the layers 23 are conducting elements forming a heater 25 to provide a local source of heat to heat the metal oxide 21 during operation of the sensor. The membrane structure 22 provides an inherent thermal insulation for the rest of the substrate with the CMOS circuit. Also, the temperature can rise rapidly around the metal oxide layer 11, while the thicker part of chip reacts due to its thermal inertia with a slower rise of temperature. By controlling the heater accordingly, the metal oxide can be heated to its operating temperature of 250 to 600 degrees Celsius.

The metal oxide layer 21 is contacted by two conductive electrodes 26 and hence acts as a resistor. In the presence of an analyte this resistance changes thereby providing a measure of the concentration of the analyte in the immediate vicinity of the metal oxide layer.

As shown in FIG. 2B there is an electrical contact 27 between electrodes 26 and at least one metallic layer of the CMOS layers 23. The contact is provided by etching a hole 28 through the top layers of the CMOS layers 23 and insulating the hole and metalizing it to form the contact. The heater 25 is connected in a similar manner to an electrically conductive layer of the CMOS layers 23.

Hence the same on-chip CMOS circuit can provide read-out of the resistance across the oxide layer 21 and control the heater 25.

The sensor typically registers changes in the resistance of the oxide material, which with an appropriate calibration can be interpreted as either the presence or the absence of acetone or generally ketones in the breath.

The presence or the absence of acetone and/or its concentration can be already a useful information for a user of the portable device as acetone concentrations are know to be indicators of metabolic processes or conditions such as diabetes. However, for other application such as monitoring fitness or weight loss, the acetone concentration in itself may not be considered a useful parameter. In such a case, the device is adapted to convert the signals relating to acetone presence or concentrations into values relating to body fat burning such as an estimated rate of fat burning.

This conversion may include the application of user specific values such as BMI, age, gender etc. to render the conversion more accurate.

Figure 3:
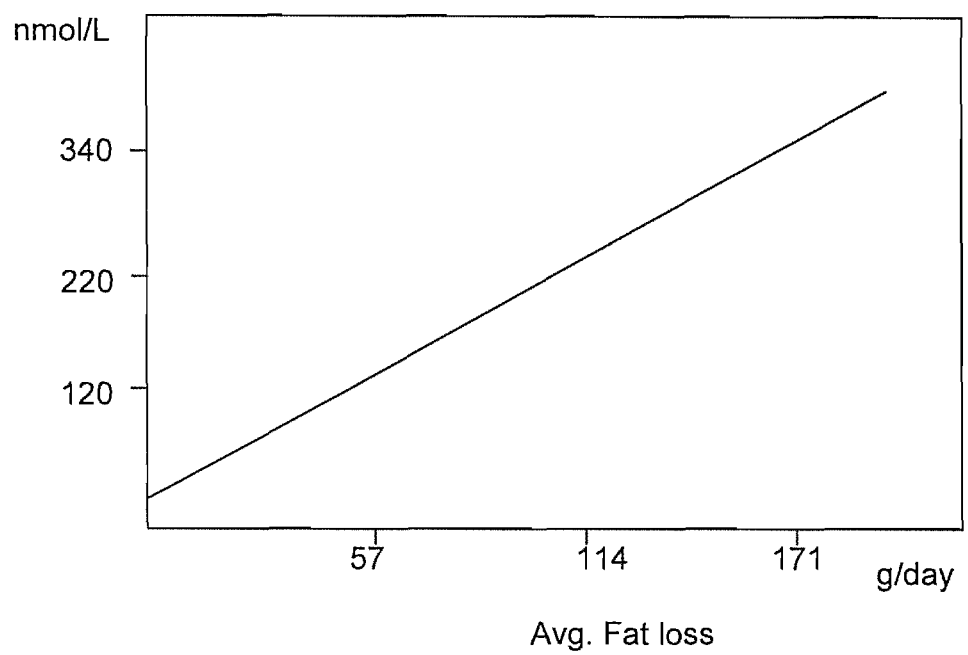
FIG. 3 illustrates a correlation between acetone and fat burning.

Whilst it is in principle possible to apply any correlation between fat burning and ketone concentration, there are known linear approximations of such correlation, which can be used in a portable device without adding a large computational overhead to the measurements. FIG. 3 illustrates such a linear relationship based on measurements of S. K. Kundu et al. as cited above with acetone concentrations in nmol/L in the breath and approximate fat burn rate in g/day.

As the device is designed to perform breath analysis tubeless, i.e. without forcing the user to touch a part of it with his lips, the device can further include sensors and/or compensators which correct for dilution of the breath by the surrounding air. The compensator can be for example part of the control circuit on the same substrate. Alternatively or in addition, a processing unit of the portable device can be programmed to perform the steps required for the compensation.

A compensation for dilution can be made using for example the inverse of the ratio of partial pressures of water $(Pm(H2O)-Pa(H2O))/(Po(H2O)-Pa(H2O))$ in the sample or any equivalent thereof to correct the measurement to represent a closer approximation of the true value. The partial pressures for water Pm(H2O) can be measured by an additional humidity sensor (not shown). The ambient humidity Pa(H2O) is assumed to be constant for a time period around the time of the actual sampling and can be determined before or after the measurement of the breath sample. The partial pressure of water in the breath Po(H2O) is known to be very reproducible and corresponds to the vapor pressure of water at 34° C.

Other compensation parameters can be applied to the measurement to compensate for the effects the size of the opening and the volume behind it has on the measurements. Considering that the opening through which the air has to pass to reach the site of the gas sensor is very small with area sizes of approximately 10 square millimeters or 3.1 square millimeters or even less, and further that the volume in which the sensor is housed is typically less than 1 cubic centimeter, a correction can be made for offsets in the amplitude of the measurement and/or for its time development during the sampling.

To compensate for these distortions in the measuring process, the compensator can apply for example a correction to determine a concentration Ci outside the opening from the concentration Cm as measured within the housing in accordance with the equation $$Ci=\gamma Cm\, f(t).$$

The first function $\gamma$ represents the balance between the diffusion of the measured component to the chemical sensor and its reduction or consumption due to a reaction at the sensor and f(t) is a time-dependent function representing geometrical constraints and which approaches 1 at long time intervals. These functions can be derived for example from a mass balance equation and a diffusion model.

While there are shown and described presently preferred embodiments of the invention, it is to be understood that the invention is not limited thereto but may be otherwise variously embodied and practised within the scope of the following claims.

The invention claimed is:

1. A portable electronic device with an integrated chemical sensor sensitive to ketones within a breath sample of a user wherein the sensor comprises at least one metal oxide gas sensor and a control circuit for the sensor integrated onto a common substrate or package, wherein the sensor is located within a duct communicating through an outer shell of the device by an opening of less than 10 mm$^2$ area.

2. The portable electronic device according to claim 1, wherein the ketones include acetone.

3. The portable electronic device according to claim 1, wherein the metal oxide sensor is a sensor including tungsten oxide as active material.

4. The portable electronic device according to claim 3, wherein the metal oxide sensor is a sensor including silicon doped tungsten oxide as active material.

5. The portable electronic device according to claim 1, further comprising a converter for converting a measurement representative of ketone concentration into a measurement representative of a metabolic ketosis or fat burning of the user.

6. The portable electronic device according to claim 1, further comprising a display with driver for displaying a signal representative of the presence of ketones or fat burning on the display of the device.

7. The portable electronic device according to claim 1, further comprising a compensator for compensating for the effect of variations in the amount of exhaled breath reaching the sensor location.

8. The portable electronic device according to claim 7, wherein the compensator corrects for dilution or the effects of the opening of the duct and volume restricting diffusion between the mouth or nose of the user and the location of the chemical sensor.

9. The portable electronic device according to claim 1, wherein the control circuit on the same substrate includes a CMOS circuit.

10. The portable electronic device according to claim 1, being selected from a group comprising:
   a mobile phone,
   a handheld computer,
   an electronic reader,
   a tablet computer,
   a game controller,
   a pointing device,
   a photo or a video camera,
   a digital music player,
   a wrist watch,
   a key fob,
   a head set, and
   a computer peripheral.

11. A portable electronic device according to claim 1, with telecommunication capabilities to allow for data and/or voice communication via private or public networks.

* * * * *